United States Patent [19]

Klingenberg

[11] 4,378,624

[45] Apr. 5, 1983

[54] SCALPEL BLADE REMOVER

[75] Inventor: Roger E. Klingenberg, Wollaston, Mass.

[73] Assignee: Braintree Scientific, Inc., Braintree, Mass.

[21] Appl. No.: 234,479

[22] Filed: Feb. 17, 1981

[51] Int. Cl.³ .......................................... B23P 19/04
[52] U.S. Cl. ...................................... 29/239; 29/267
[58] Field of Search ................. 29/270, 267, 239; 269/236, 15; 254/28

[56] References Cited

U.S. PATENT DOCUMENTS

| 1,321,627 | 11/1919 | Hagstrom | 269/236 |
| 1,883,335 | 10/1932 | Braders | 269/236 |
| 3,598,164 | 8/1971 | August | 269/15 |
| 4,055,880 | 11/1977 | Moessner | 29/267 |
| 4,153,238 | 5/1979 | Tabor | 269/15 |

Primary Examiner—James L. Jones, Jr.
Attorney, Agent, or Firm—Kenway & Jenney

[57] ABSTRACT

A scalpel blade remover in which the blade is clamped against a fixed block by manipulating a lever to cause a movable block to move toward the fixed block. The movable block is preferably made of resilient material and all other elements of the structure are made of metal such as stainless steel, all components being autoclavable. A tab is provided on the movable block to engage an end of the blade and move that end relative to the body of the blade and the scalpel handle to disengage the blade from the handle. The blocks are mounted upon a supporting surface, beneath which a sterile disposable box may be disposed. The supporting surface is slotted in a plane which includes the area of clamping of the scalpel blade between the fixed and movable blocks. The movable block may also be provided with a guide portion to ensure the clamping action, and the movable block may be provided with a relieved or cut-off end permitting a scalpel blade to be disengaged from the scalpel handle.

10 Claims, 4 Drawing Figures

SCALPEL BLADE REMOVER

BACKGROUND OF THE INVENTION

Surgical scalpels are used for a variety of purposes, in research laboratories, schools, veterinary clinics, and, of course, hospitals. The present invention is concerned with the widely used type of scalpel which consists of a sturdy reusable handle to which a disposable blade may be attached. Depending upon the purpose for which the scalpel is to be used, the blade may have any of a number of shapes and sizes.

Because the present invention is primarily concerned with protecting the user of a scalpel from injury, it is applicable to any procedure where a surgical scalpel is utilized, but it is of particular value in hospitals. A sharp edge is essential in conducting a surgical operation. However, blades tend to lose their edge very quickly in such procedures and, worse yet, frequently are contaminated by the tissue being cut by the blade. It is common to use many blades during a single surgical procedure. Thus, removal of a used blade from the handle and replacement of the blade with a new sterile blade is a frequent occurrence in the course of a surgical procedure. The design of scalpels requires, for obvious reasons, that the blade be firmly attached to the handle. To insure such a firm attachment, most scalpel blades are locked to the handle by a simple catch mechanism. To remove a used blade requires a skillful release of the catch and a pull on the blade. In fact, the technique ordinarily requires grasping the blade with a locking forceps and twisting it to release the catch. When the catch is released, the blade may be pulled away from the handle. Pulling or snapping the blade away from the handle in this fashion exposes both the person changing the blade and anyone nearby to the possibility of an accidental cut. A wound produced by such an accidental cut is particularly serious because the wound is likely to become contaminated by the used blade and an infection may well set in.

It is a primary object of the present invention to reduce or substantially eliminate the risk of changing scalpel blades.

It is a further object of the present invention to simplify the removal of a scalpel blade from its handle.

A still further object of the present invention is a completely autoclavable and chemically inert device for the removal of scalpel blades.

Still another object of the present invention is to facilitate the disposal of used scalpel blades, direct handling of used blades being avoided at every stage of the disposal process.

SUMMARY OF THE INVENTION

In a preferred form, the present invention is embodied in a rugged stainless steel base on which a fixed and a movable block are mounted. One of the blocks, preferably the fixed block, is made of stainless steel, and the other or movable block is preferably made of Teflon. The user holding the scalpel by its handle inserts the blade between the clamping blocks in a position determined by a stop formed on the clamping blocks. The handle is then lowered until the blade lies along and against the fixed block. The movable clamping block is then moved toward the fixed block by means of a lever pivotally mounted on the supporting base and having a camming surface bearing upon the movable block until the blade is clamped between the blocks. A tab projecting from the end of the movable block engages the lower rear corner of the blade, causing the blade to be disengaged from the catch formed on the handle for holding the blade. The scalpel handle is then pulled away from the clamping blocks, leaving the blade in the clamping plane. The lever is then returned to its original position and the used blade drops through a slot formed in the supporting base into a sterile disposal box. The disposal box is removable from the support base to be discarded with the used blades. For a better understanding of the present invention together with other objects, features and advantages, reference should be made to the following description of a preferred embodiment which should be read in conjunction with the attached drawing which includes the figures listed below.

DESCRIPTION OF PREFERRED EMBODIMENT

Figure 1:
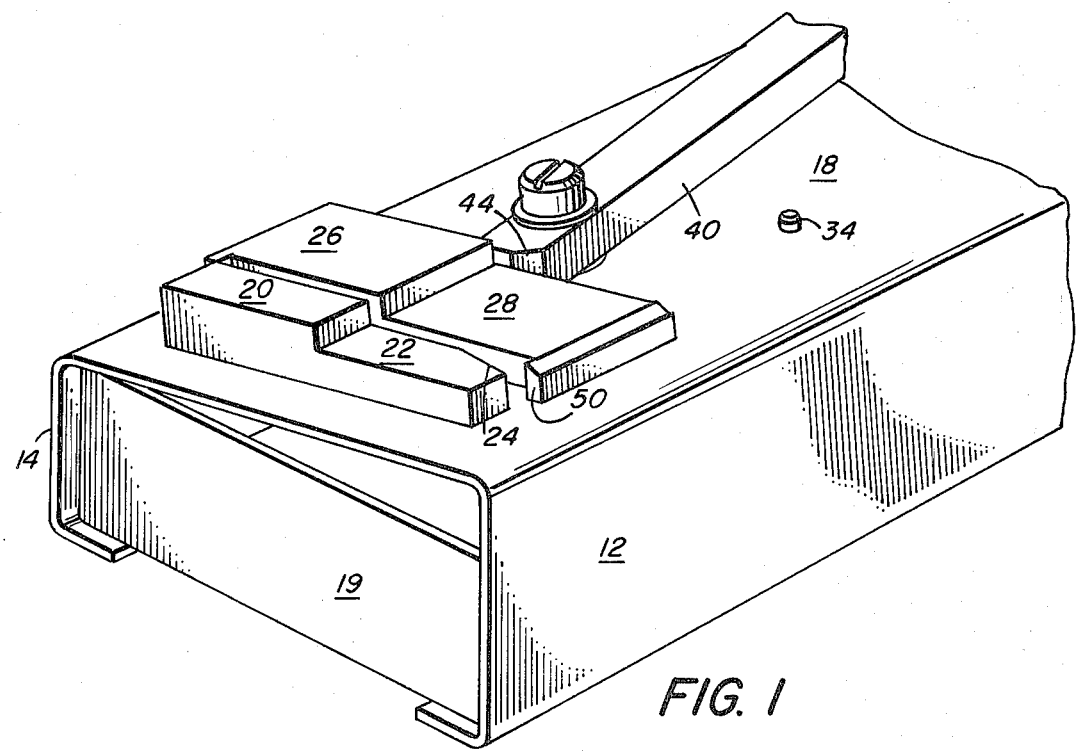
FIG. 1 is a fragmentary perspective view of a scalpel blade remover built in accordance with the present invention.
Figure 2:
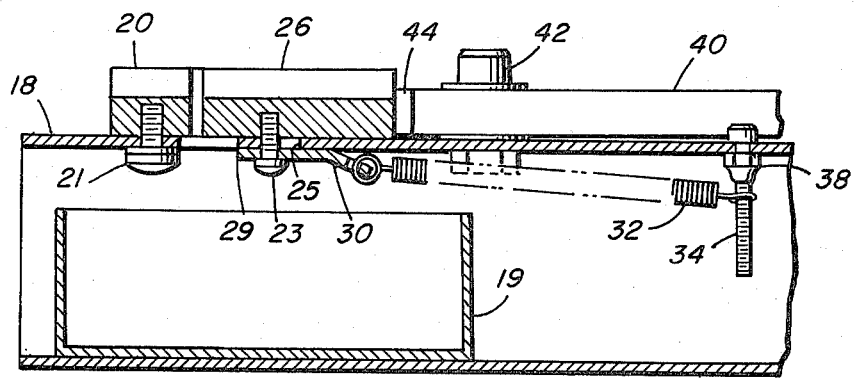
FIG. 2 is a view in section taken along the lines 2—2 of FIG. 1.

In FIGS. 1 and 2 there is shown a support base 12 formed of stainless steel of about 16 gage. The steel sheet may be bent into a generally rectangular form, although for convenience of the user, the side member 14 may be shorter than the side member 16 in order that the top surface 18 may be at an angle to the horizontal. Having the top surface 18 at an angle to the horizontal provides a degree of convenience to the user as will be explained hereinbelow.

A disposal box 19 may be fitted into the open volume formed beneath the surface 18 of the support block 12. The box may be open-topped or slotted.

Mounted adjacent one end of the support base 18 is a fixed block of stainless steel 20. The block 20 may be held in place by any convenient means, such as screws of the type shown at 21. The block 20 preferably includes a lower stepped portion 22, the end of which is cut away diagonally, as at 24. A movable block 26 which includes a lower stepped portion 28 is slidably mounted on the surface 18 by means of screws such as the screws 23. The mounting screws for the slidable block are threaded into the slidable block through longitudinal slots such as the slot 25 formed in the surface 18. The screws also pass through a tongue 29, holding the tongue in slidable relationship to the underside of the surface 18.

Spacers in the form of stainless steel washers on the screws may be used to provide clearance between the tongue and the underside of the surface 18. The tongue 29 has a downwardly inclined end 30 to which tension springs such as the spring 32 are attached. The opposite ends of the springs such as the spring 32 are fixed to screws such as the screw 34. The screw 34 is locked in place on the underside of the surface 18 by means of a lock nut 38. Generally, the spring assemblies, which include the screws, lock nuts and tension springs, are two in number and spaced apart in parallel relationship below the surface 18.

A lever arm 40 is pivotally attached to the top surface 18 by means of a pivot screw 42. One end 44 of the lever 40 is formed into a cam surface. The cam surface bears against a side of the movable block 26 to impart motion thereto in response to pivotal movement of the lever 40. The action of the spring assemblies maintains the side surface of the movable block 26 in contact with the cam surface 44.

Figure 3:
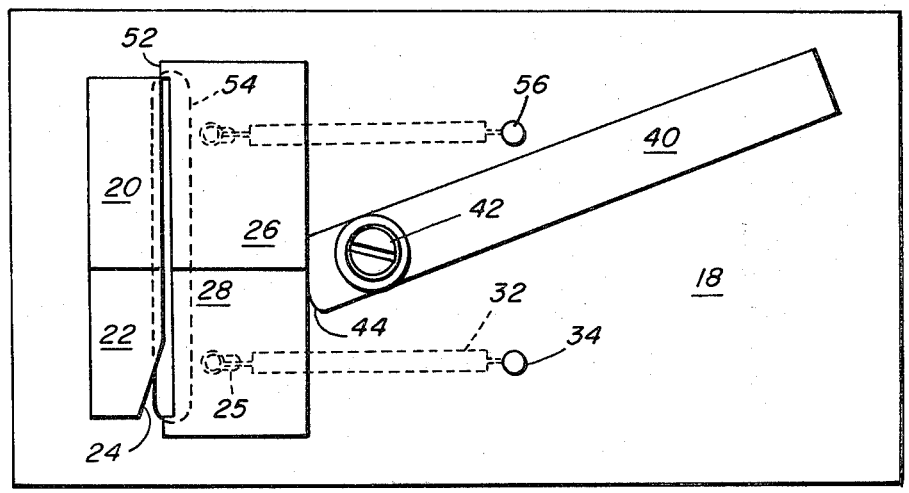
FIG. 3 is a top view of the device shown in FIG. 1.

Visible in FIG. 1 but better seen in FIG. 3 is an end tab 50 formed at the lower stepped end 28 of the movable block. A second guide tab 52 is formed at the opposite end of the movable block 26. In FIG. 3, there is shown a slot 54 which is formed in the support block surface 18 beneath the plane of contact of the movable block 26 with the fixed block 20. Also visible in FIG. 3 is the screw 34 to the lower end of which the tension spring 32 is anchored. A similar anchoring screw 56 for another spring assembly is also shown.

The cam surface 44 and its contact with the side of the block 26 are also visible in FIG. 3 and, as indicated by the curved arrow, when the lever 40 is moved in a clockwise direction, the cam surface 44 causes the movable block 26 to move into contact with the fixed block 20. The guide tab 52 serves to align the clamping surfaces of the two blocks when the lever 40 is manipulated.

Figure 4:
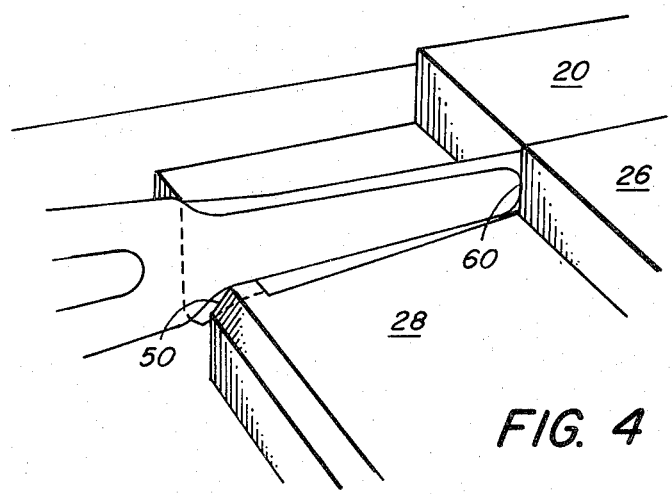
FIG. 4 is a blown-up view of an unlocking key used in one version of the present invention.

FIG. 4 illustrates the action of the scalpel blade remover when a scalpel having a locking catch is used. The blades of scalpels of other designs having different catches may also be removed utilizing the device illustrated, but in the more common scalpels, the unlocking tab is particularly useful. With such common scalpels, the blade is inserted between the blocks as shown in FIG. 4 until the handle tip 60 contacts the upper stepped portion 26. The off-horizontal disposition of the surface 18 facilitates the insertion of the blade. The handle is then lowered until the rear corner of the blade is adjacent the unlocking key 50. The operator then pulls the lever in a counterclockwise direction, bringing the movable block into contact with the scalpel blade. Further movement of the lever clamps the blade between the upper portion 20 of the fixed block and the upper portion 26 of the movable block as the unlocking key 50 pushes the rear corner of the blade out of line with the remainder of the blade as permitted by the cut-away portion 24 of the lower step 22 of the fixed block.

The locking catch is thus released and the scalpel handle may be pulled straight back, leaving the blade clamped between the fixed and movable blocks. When the lever is released, spring action carries the movable block away from the fixed block and the blade drops through the slot 54 into the disposal box 19.

The disposal box 19 may be removed and the slot in the box covered with a piece of surgical tape. The box may then be disposed of in normal ways or, should it be desired to salvage the contents of the box, the box contents may be autoclaved.

All elements of the device of the invention are preferably made of stainless steel with the exception of the movable block 26, which is made of resilient material. The preferred resilient material for the movable block is Teflon. Both stainless steel and Teflon are highly resistant to chemical attack and can withstand the relatively high temperatures required for autoclaving. A temperature of 250° F. or higher is often reached in the process of autoclaving. The materials may also be exposed to ethylene oxide or other commonly used sterilizing chemical solutions without damage to any of the elements. Any normal cleaning method utilizing a bristle brush or pipe cleaners may be employed.

What is claimed is:

1. A device for removing a scalpel blade from a handle comprising a support base, a fixed block mounted on said base, a movable block also mounted on said base, at least one of said blocks being made of resilient material, means for moving said movable block toward and away from said fixed block, movement toward said fixed block being effective to clamp said blade between confronting surfaces of said fixed and movable blocks, and means formed adjacent one end of one of said blocks to contact an end of said blade and disengage said blade from said handle, movement of said movable block away from said fixed block permitting separation of said handle from said blade.

2. A device as defined in claim 1 wherein said support base has an opening formed therein, said opening being of sufficient size for the passage therethrough of a scalpel blade and being disposed beneath the point at which said confronting surfaces of said fixed and movable blocks clamp said blade.

3. A device as defined in claim 1 wherein said means for moving said movable block toward and away from said fixed block comprises a lever pivotably supported upon said support base and having a cam surface formed thereon and resilient means for urging said movable block into contact with said cam surface.

4. A device as defined in claim 1 wherein said means on one of said blocks to disengage said blade from said handle comprises a tab formed on said movable block, said tab being disposed at one end of the confronting surface of said movable block and extending a predetermined distance outwardly therefrom.

5. A device as defined in claim 1 wherein said support base and said fixed block are formed of stainless steel and said movable block is formed of autoclavable resilient material.

6. A device as defined in claim 3 wherein said resilient means for urging said movable block into contact with said cam surface comprises at least one tension spring extending between said movable block and a point on said support base.

7. A device as defined in claim 2 wherein said support base is generally rectangular in cross-section having side members and a flat upper surface to which said fixed block is rigidly attached and on which said movable block is slidably mounted, an open volume being defined by said side members and said upper surface and further comprising an open-topped disposal box removably disposed in said open volume beneath said opening formed in the upper surface of said support base.

8. A device as defined in claim 7 wherein said side members are of unequal length, said upper surface being at an angle to the horizontal.

9. A device for removing a scalpel blade from a handle comprising a support base having a generally rectangular cross-section, an open inner volume, and a flat upper surface, a fixed block mounted on said surface, a movable block of resilient material slidably mounted on said surface, spring means normally urging said movable block away from said fixed block, a lever having a cam surface bearing upon said movable block and operative to move said movable block toward and away from said fixed block, manipulation of said lever in one direction causing said movable block to clamp said blade against said fixed block and permitting separation of said handle from said blade, a slot being formed in said upper surface in alignment with the plane of clamping of said blade, releasing of said lever in a direction opposite to said one direction permitting said spring means to cause movement of said movable block away from said fixed block and declamping of said blade, said blade then dropping through said slot.

10. A device as defined in claim 9 and further comprising an open-topped blade disposal box removably disposed in said open inner volume beneath said slot.

* * * * *